United States Patent [19]

Fournier et al.

[11] Patent Number: 5,192,287
[45] Date of Patent: Mar. 9, 1993

[54] SUTURE KNOT TYING DEVICE

[75] Inventors: Donald J. Fournier, North Providence, R.I.; Donald Rose, New Rochelle, N.Y.

[73] Assignee: American Cyanamid Company, Stamford, Conn.

[21] Appl. No.: 681,577

[22] Filed: Apr. 5, 1991

[51] Int. Cl.⁵ .............................................. A61B 17/00
[52] U.S. Cl. .................................. 606/139; 606/148; 289/17
[58] Field of Search ............... 606/139, 144, 146, 148; 289/17

[56] References Cited

U.S. PATENT DOCUMENTS

| 919,138 | 4/1909 | Drake et al. | 606/144 |
|---|---|---|---|
| 1,583,271 | 5/1926 | Biro | 606/144 |
| 1,815,725 | 7/1931 | Pilling et al. | 606/144 |
| 2,579,192 | 12/1951 | Kohl | 606/145 |
| 2,595,086 | 4/1952 | Larzelere | 128/326 |
| 3,013,559 | 12/1961 | Thomas | 606/144 |
| 3,470,875 | 10/1969 | Johnson | 606/144 |
| 3,638,653 | 2/1972 | Berry | 606/145 |
| 3,840,017 | 10/1974 | Violante . | |
| 3,842,840 | 10/1974 | Schweizer . | |
| 3,901,244 | 8/1975 | Schweizer . | |
| 3,946,740 | 3/1976 | Bassett | 128/340 |
| 4,164,225 | 8/1979 | Johnson et al. | 606/145 |
| 4,224,947 | 9/1980 | Fuduka . | |
| 4,312,337 | 1/1982 | Donohue . | |
| 4,493,323 | 1/1985 | Albright et al. . | |
| 4,509,516 | 4/1985 | Richmond . | |
| 4,596,249 | 6/1986 | Freda et al. . | |
| 4,597,390 | 7/1986 | Mulhollan et al. . | |
| 4,602,635 | 7/1986 | Mulhollan et al. . | |
| 4,614,187 | 9/1986 | Mulhollan et al. . | |
| 4,621,640 | 11/1986 | Mulhollan et al. . | |
| 4,643,178 | 2/1987 | Nastari et al. . | |
| 4,781,190 | 11/1988 | Lee . | |
| 4,836,205 | 6/1989 | Barrett . | |
| 4,890,615 | 1/1990 | Caspari et al. | 606/146 |
| 4,923,461 | 5/1990 | Caspari et al. | 606/146 |
| 4,961,741 | 10/1990 | Hayhurst | 606/139 |
| 5,084,058 | 1/1992 | Li | 606/148 |
| 5,087,263 | 2/1992 | Li | 606/148 |

FOREIGN PATENT DOCUMENTS

| 185025 | 7/1955 | Austria . | |
|---|---|---|---|
| 912619 | 5/1954 | Fed. Rep. of Germany | 606/139 |
| 1169630 | 7/1985 | U.S.S.R. | 606/139 |

OTHER PUBLICATIONS

Brochure: Acufex Linear Instruments, 1989.
Brochure: Acufex Rotary Instruments, 1989.

Primary Examiner—Stephen C. Pellegrino
Assistant Examiner—Gary Jackson
Attorney, Agent, or Firm—D. E. Denninger

[57] ABSTRACT

A surgical device (20) used to tie knots in sutures is disclosed. The device has a stationary leading member (42) and a sliding trailing member (44), together with a mechanism (26, 102) for sliding the trailing member relative to the leading member. One knot (90) of the suture is placed against the end of the leading member (42) and a second knot (92) is placed against the end of the trailing member (44). The two knots are slid into place with the first knot being held in position against the tissue and the device (20) is acutated to slide the trailing member together with the second knot into position tightly against the first knot.

9 Claims, 3 Drawing Sheets

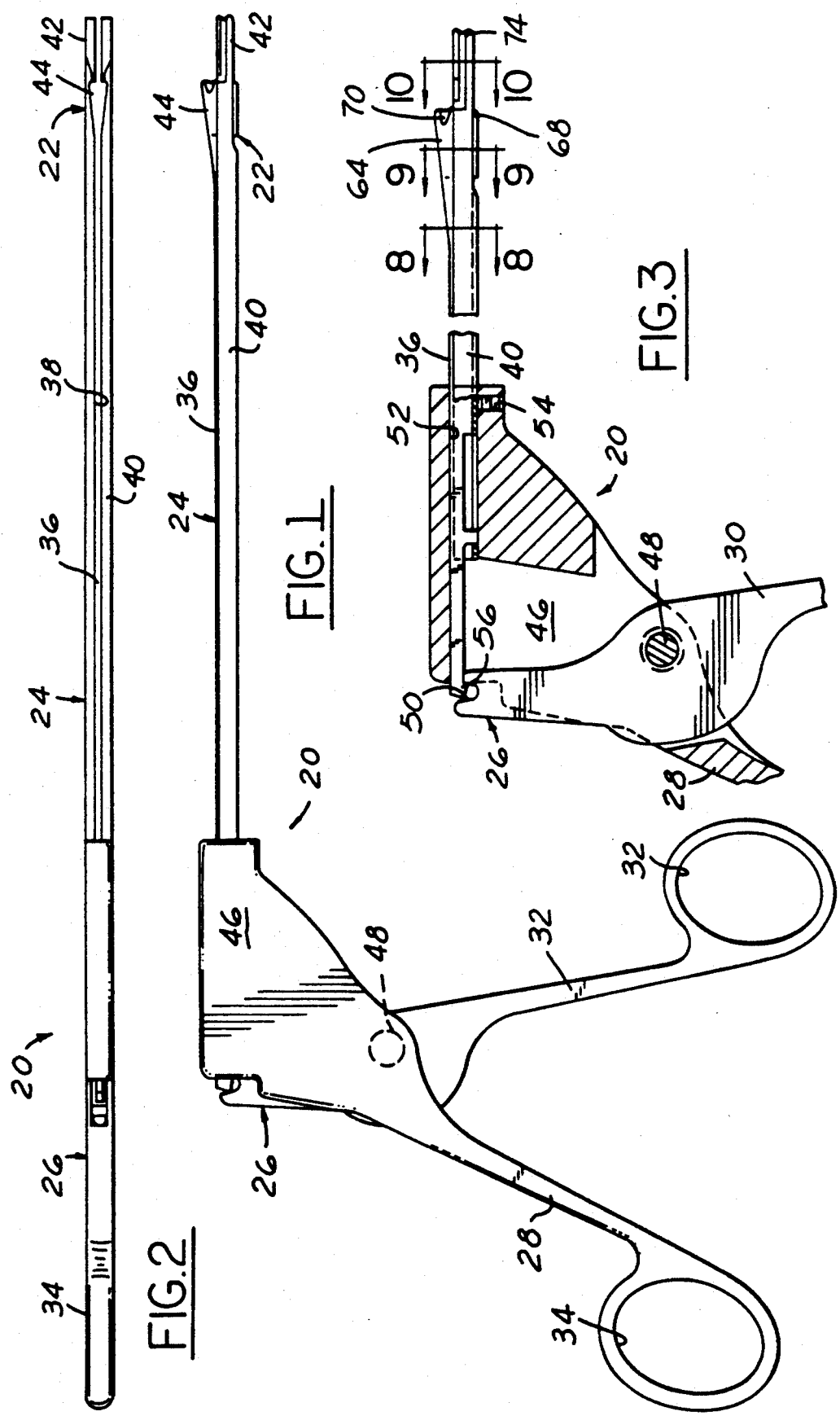

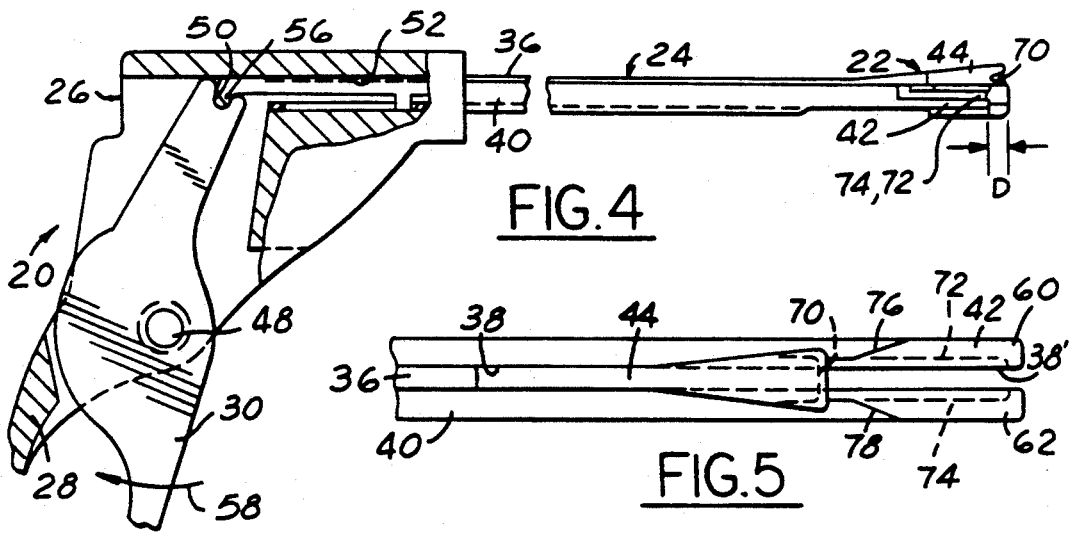
FIG.4
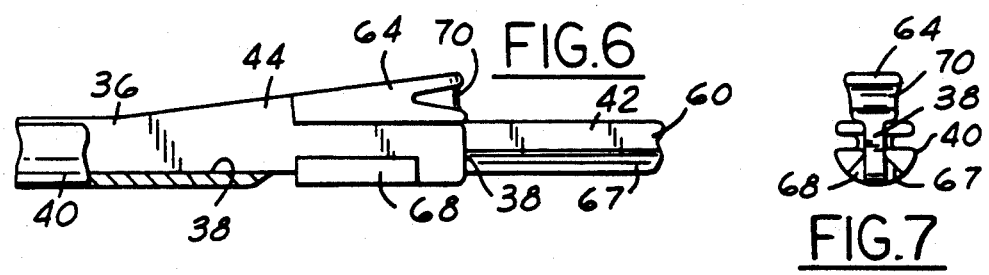
FIG.5
FIG.6
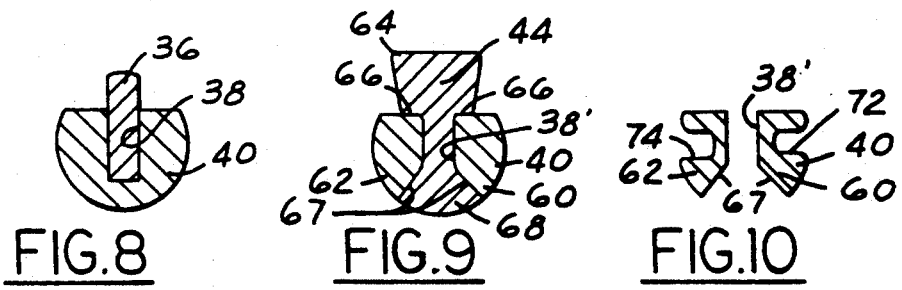
FIG.7
FIG.8 FIG.9 FIG.10
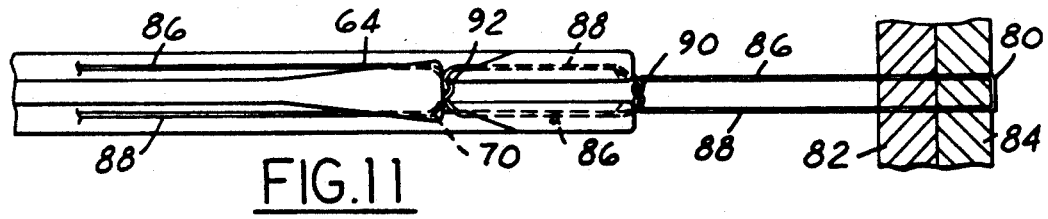
FIG.11
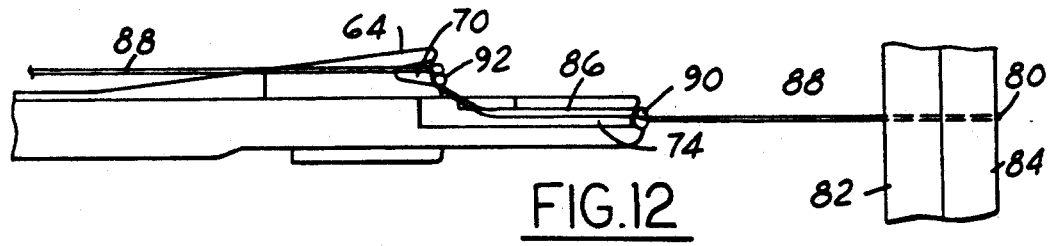
FIG.12

SUTURE KNOT TYING DEVICE

TECHNICAL FIELD

A device for tying knots in sutures during surgery is disclosed. The device has a stationary member which holds a first one-half knot in position and a movable member which slides a second one-half knot tightly against the first knot forming a tight complete knot. The device has an elongated arm to allow it to be positioned through a cannula during arthroscopic surgery.

BACKGROUND OF THE INVENTION

Arthroscopic surgery is in common use to repair or reconstruct torn or detached ligaments and soft tissue or cartilage in joints. Injuries to joints are a frequent occurrence today, particularly with the modern emphasis on sports and other physical activity.

Many common joint injuries occur in the knee and shoulder joints. In order to repair torn or detached tissue in these joints, arthroscopic surgery is typically used. This surgery is less invasive and traumatic to the patient and results in faster recovery times and less scarring.

Arthroscopic surgery is difficult and time consuming. Most of the work is done in the joint with illumination and surgical instruments being passed through cannulas positioned in small openings in the skin. In order to allow the surgeon to work in these limited spaces, instruments with elongated arms or shafts have to be used.

Often during these procedures, sutures are used to hold ligaments or other soft tissue in position until it is reattached or healed. Since the tissue to be reattached has to be accurately positioned in order to permit the joint to function again as normally as possible, the sutures have to be accurately placed and tightly held in position.

It is often difficult to tie knots tightly in sutures in joints which are being operated on arthroscopically. Either an instrument has to be passed down the cannula to form and tie the knot at the desired site, or the knot has to be formed outside the cannula and pushed down the suture (through the cannula) into position.

Prior devices or systems used to tie suture knots during arthroscopic surgery are shown in U.S. Pat. Nos. 4,602,635 to Mulhollan et al; 4,923,461 to Caspari et al. and 4,961,741 to Hayhurst et al.

It is an object of the present invention to provide an improved instrument which ties knots in sutures during surgery. It is another object to provide an improved instrument which ties knots inside joints during arthroscopic surgery.

It is a further object of the invention to provide a knot tying instrument which is simple to use and which can be used quickly and easily. It is still another object of the invention to provide an instrument which forms and tightly ties knots in sutures in position during surgery.

It is still a further object of the invention to provide a unique and improved method for tying knots in sutures during surgery, particularly arthroscopic surgery.

These and other objects are met by the present invention which will become apparent upon review of the following detailed description of the invention in view of the drawings.

SUMMARY OF THE INVENTION

The present invention utilizes a unique surgical instrument to provide a unique method of tying a knot in a suture during surgery. The instrument is a knot tying device having an elongated movable shaft member positioned adjacent an elongated fixed shaft member, the two shaft members having suture holding grooves at their forward ends. An actuation mechanism, either a linear-type or syringe-type mechanism is used to slide the movable shaft member relative to the fixed shaft member and actuate the knot tying mechanism.

A loose knot is tied in the two ends of a suture which has been inserted in position by the surgeon. The suture is situated on the unique device with the first one-half knot positioned in the groove on the forward end of the fixed shaft member and the second one-half knot positioned in the groove on the forward end of the movable shaft member.

Movement of the entire knot tying device toward the site of the knot while keeping tension on the loose ends of the suture, positions the first one-half knot in the appropriate position. Activation of the actuation mechanism slides the movable shaft member and second one-half knot into final position adjacent the first one-half knot. Continued tension of the suture sets the final knot in place.

BRIEF DESCRIPTION OF THE DRAWINGS

FIG. 1 is a side elevational view of the preferred embodiment of the inventive knot tying device;

FIG. 2 is a top view of the device of FIG. 1;

FIG. 3 is a partial cross-sectional view of the device showing the actuation mechanism;

FIG. 4 is a view similar to FIG. 3, but after actuation of the mechanism;

FIG. 5 is an enlarged top view of the forward end of the device;

FIG. 6 is an enlarged partially broken away side elevational view of the forward end of the device;

FIG. 7 is an end elevational view of the forward end as shown in FIG. 5;

FIGS. 8, 9 and 10 are cross-sectional views of the invention taken along lines 8—8, 9—9 and 10—10, respectively, of FIG. 3;

FIGS. 11 and 12 are two elevational views showing the use of the present invention with the knot loops positioned on it;

BEST MODE(S) FOR CARRYING OUT THE INVENTION

Figure 13:
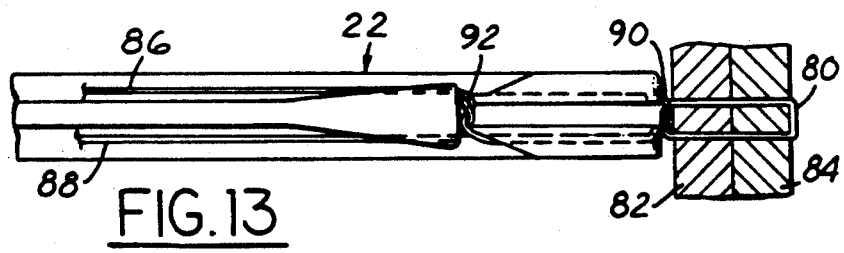
FIGS. 13 and 14 are two elevational views showing use of the present invention with the knot loops positioned on it and moved to the appropriate site.

A preferred form of the invention suture knot tying device 20 is shown in FIGS. 1 and 2. The device 20 has an operating knot tying forward end 22, an elongated shaft or arm 24, and an actuation mechanism 26. The actuation mechanism is operated by two scissor-type loop handle members 28 and 30 which are provided with finger openings 32 and 34, respectively, for manual actuation.

The knot tying device has two elongated rigid members forming the shaft and forward end. A thin elongated movable shaft member 36 is slidingly positioned in a channel 38 in an elongated fixed shaft member 40 (see also FIG. 8).

The fixed member 40 has a leading end 42 and the movable member 36 has a trailing end 44. Together the leading end 42 and trailing end 44 comprise the forward end 22 of the device 20 and the details and operation are described in more detail below.

The knot tying device 20 is preferably made of an autoclavable metal, such as stainless steel, but it is understood that it can be made of any comparable material. An alternative design, for example, could be manufactured using thermoplastic materials. The stainless steel should be a surgical grade material, such as 17–4.

The preferred actuation mechanism for the invention is a loop handle linear-type mechanism which is commonly used for many surgical instruments. The operation of the actuation mechanism 26 is shown in FIGS. 3 and 4. One handle member 28 is formed as part of housing 46 and the other handle member 30 is movably mounted inside housing 46 and connected to it by pivot member 48. The elongated fixed shaft member 40 is positioned in bore 52 in the housing 46 and held firmly in place by set screw 54.

One end of member 30 has finger opening 32 and the other end has a U-shaped or notched opening 50. The end of the elongated movable shaft member 30 which is positioned inside housing 46 has a hook member 56 which is situated within U-shaped opening or notch 50.

As shown by a comparison of FIGS. 3 and 4, the knot tying device is actuated by manual movement of member 30 in the direction of arrow 58 toward member 28. As member 30 rotates around pivot 48, the movable shaft member 36 is slid along the channel 38 in the stationary shaft member 40 due to the interconnection of the hook member 56 and the notch 50. When the movable shaft member 36 is slid fully to its shifted position (as shown in FIG. 4), the front of the trailing end 44 protrudes or extends a distance "D" beyond the front of the leading end 42.

The structure of the ends of the shaft members forming the forward end 22 is shown in enlarged form in FIGS. 5–10. In the leading end 42 of the stationary shaft member 40, the channel 38 opens up into a space 38' between opposite prong members 60 and 62. The channel 38 and space 38' guide the movable shaft member 36 along its entire path of travel.

The forward end 44 of the trailing member 36 has an enlarged protruding head 64 which extends above the fixed shaft member 40. The head has a pair of shoulders 66 which rest on the upper surface of shaft member 40. Positioned below the head 64 is a flange member 68 which in cooperation with the angled sides 67 of space 38' and the relationship of shoulder 66 and shaft member 40, keep the forward end 44 in precise lateral position in the space 38'.

A suture groove 70 on the head 64 extends along the forward face of the head and wraps around the two sides. The groove 70 acts to hold the suture and knot in position on the head 64 when the knot tying device 20 is utilized.

The forward or leading end 42 of the fixed shaft member 40 has a pair of grooves 72 and 74 extending along the front and side surfaces of the prong members 60 and 62. These grooves 72 and 74 act to hold the suture and knot in position on the head 64 when the device 20 is utilized. The grooves 72 and 74 also have a depth sufficient to securely hold the sutures in place and prevent them from being dislodged when the device is inserted through a cannula and into position in the joint.

The upper surfaces 76 and 78 of the prongs 60 and 62 are angled back towards the axis of the shaft member 40, as shown in FIGS. 2, 5 and 11–14. This allows the sutures positioned in grooves 72 and 74 to be passed around and form a knot in the groove 70 on the forward face of the head 64 of the movable trailing shaft member 36.

The operation of the knot tying device is shown in FIGS. 11–17. The device 20 is used after a suture has been looped or passed through the tissue or ligament and the two loose ends are pulled out of the cannula. The placement of a suture 80 is shown in representative form in FIGS. 11–17. The suture 80 is passed through two pieces of tissue 82 and 84 which are being held together, for example, in order to be reattached to one another. It is understood, of course, that the present invention can be used to tie knots in sutures which are placed in numerous and various locations and for various purposes.

The suture 80 is placed through the pieces of tissue 82 and 84 by any conventional means. The two loose ends 86 and 88 of the suture are then grasped and pulled out through the end of the arthroscopic cannula (not shown) again by any conventional means.

When the suture is ready to be tied into a knot, a loose square knot is formed with the two loose ends outside the cannula. The suture ends are looped one over the other to form a first loop or one-half knot 90 and then looped one over the other in the opposite direction to form a second loop or one-half knot 92. The forward end 22 of the device is then pushed into the pair of one-half knots with the one-half knot 90 being positioned in the groove on the front face of the prong members 60 and 62, and with the other one-half knot 92 being positioned in the groove 70 in the head 64. In this regard, it may be necessary to rotate the device 20 relative to the suture in order to place the one-half knot 92 in the groove 70.

As shown in FIGS. 11 and 12, the portion of the suture ends 86 and 88 which extend between the two loops or one-half knots are positioned in grooves 72 and 74. The suture ends are passed around the angled surfaces 76 and 78' to allow the second one-half knot to rest in groove 70. The loose ends 86 and 88 of the suture are pulled tightly along the shaft toward the actuation mechanism 26 and held with a suture clamp (not shown).

As tension is held on the two loose ends 86 and 88, the forward end of the device 20 is slid down the suture toward the tissue 82 and passed through the cannula. The loops or one-half knots 90 and 92 slide easily down the length of the suture as the device is pushed toward the tissue and as tension is held on the suture ends. The present invention works equally well on both braided and monofilament sutures.

Figure 14:
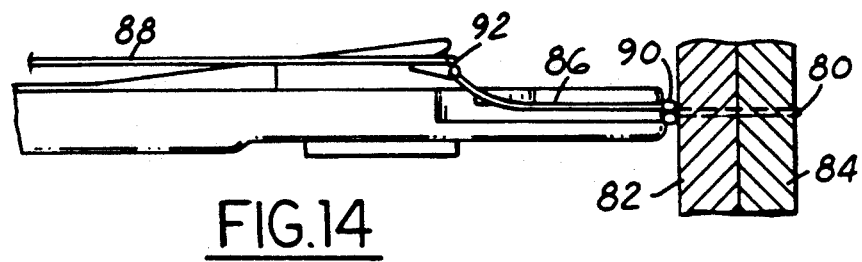

The device with the suture on it is pushed into the joint until the forward one-half knot 90 is pushed tightly against the tissue 82. This is shown in FIGS. 13 and 14.

In order to assist the sliding movement of the instrument along the suture, the forward ends of the two shafts (particularly where they might make contact with the sutures) are coated with an anti-stick material.

Suitable materials for this purpose are Teflon and teflon-like substances, as well as Nicotel and nickel-based substances.

Figure 15:
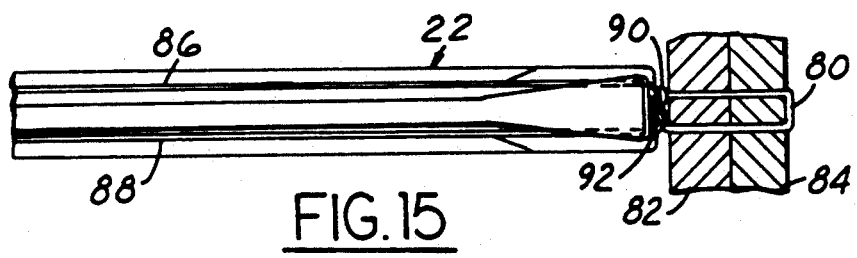
FIGS. 15 and 16 are two elevational views illustrating the tightening of a knot by use of the present invention.
Figure 16:
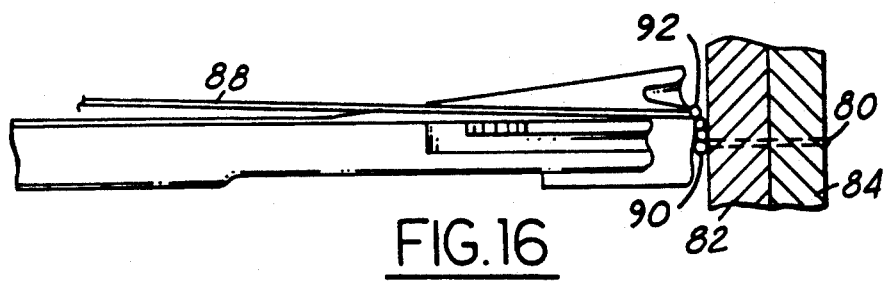

The activation of the actuation mechanism 26 slides the movable shaft member 36 forwardly relative to the fixed shaft member 40 and in turn advances the trailing one-half knot 92. When the front surface of the movable shaft member 36 is approximately even with the front surface of the fixed shaft member 40, the full or complete knot is first formed. This is shown in FIGS. 15 and 16.

Further actuation of the actuation mechanism 26 moves the forward end of the shaft member 36 the distance "D" (FIG. 4) beyond the end of the fixed shaft member and, together with increased tension on the suture ends 86 and 88 tightly sets the two one-half knots 90 and 92 together one on top of the other forming the completed knot 94.

Figure 17:
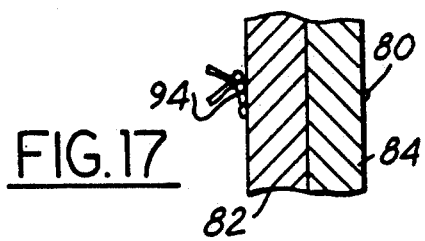
FIG. 17 shows a knot after being moved, held and tightened in position by use of the present invention.

After the knot tying device 20 is removed from the joint and cannula, the loose ends of the suture are trimmed off adjacent the knot (as shown in FIG. 17), using conventional instruments and methods.

In accordance with the scope of the present invention, it is to be understood that the relative positions of the movable and fixed shaft members could be reversed and that other modifications could be made. For example, the fixed shaft member could be positioned inside an outer movable shaft member, or the two shaft members could be positioned side-by-side (and keyed together in some manner). In addition, the outer fixed shaft member 40 as shown in FIGS. 1–17 could be a hollow tube for most of its length and the movable shaft member 36 could be coaxially positioned inside it in a telescoping relationship. Finally, other means for moving one shaft member relative to the other could be employed.

Figure 18:
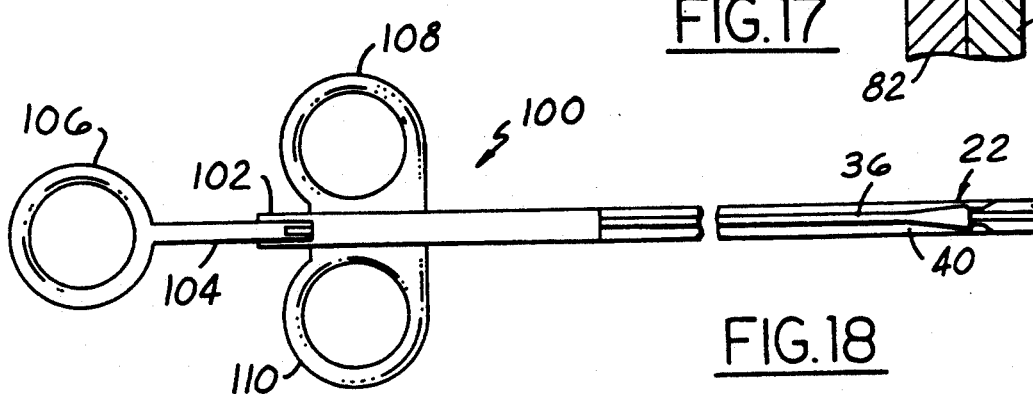
FIG. 18 illustrates another embodiment of the invention.

An alternate embodiment of the invention is shown in FIG. 18. In this embodiment, the knot tying device 100 has a syringe-type activation mechanism 102 for activating the knot tying mechanism. All of the remaining parts of this embodiment are the same as those described above with reference to the linear actuator-style device shown in FIGS. 1–17. The steps and method used to tie the knot and secure it in place are also the same. The only difference is the actuation mechanism used to move the elongated movable shaft member 36 relative to the elongated fixed shaft member 40.

In the activation mechanism 102, an extension plunger or shaft 104 is connected directly to shaft member 36. A loop or finger grip 106 is attached to the end of shaft 104 for ease of manipulation and use by the surgeon. A pair of loops or finger grips 108 and 110 are connected to the fixed barrel or shaft member 40 and used to hold the shaft securely when movement of the sliding shaft 36 is required.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

It is claimed:

1. A device for tying knots in a suture, comprising:
    a stationary shaft member having at least first and second fixed prongs at its distal end;
    a movable shaft member having a distal head and being slidable between said first and second prongs from a proximal, retracted position to a distal, extended position;
    actuation means for moving said movable shaft member from said retracted position to said extended position;
    said first and second prongs defining first and second grooves, respectively, each said groove extending along a front surface and a distal part of an outer side surface of said respective prong;
    said distal head of said movable shaft member defining a third groove; and
    said first and second grooves being shaped to guide a first one-half knot in the suture, and said third groove being shaped to guide a second one-half knot which is tightened against the first one-half knot to form a full knot when said movable shaft member is slid to said extended position.

2. The device of claim 1 wherein said third groove is spaced from the longitudinal axis of said stationary shaft member to lie above said first and second grooves.

3. The device of claim 1 wherein said first and second prongs each define, above a proximal portion of said first and second grooves, respectively, an angled upper surface which is angled back toward the longitudinal axis of said stationary shaft member.

4. The device of claim 1 wherein said movable shaft member is positioned in a longitudinal channel in said stationary shaft member.

5. The device of claim 1 wherein said actuation means is a linear-type mechanism.

6. The device of claim 1 wherein said actuation means is a syringe-type mechanism.

7. The device of claim 1 wherein said distal head passes distal to said stationary shaft member in said extended position.

8. A device for tying knots in a suture comprising:
    a stationary shaft member having at least first and second fixed prongs at its distal end;
    a movable shaft member having a distal head and being slidable between said first and second prongs from a proximal, retracted position to a distal, extended position;
    actuation means for moving said movable shaft member from said retracted position to said extended position;
    said first and second prongs defining first and second grooves, respectively, each said groove extending along a front surface and a distal part of an outer side surface of said respective prong, said first and second prongs further defining an angled upper surface which is angled back toward the longitudinal axis of said stationary shaft member above a proximal portion of said first and second grooves, respectively;
    said distal head of said movable shaft member defining a third groove which is spaced from the longitudinal axis of said stationary shaft member to lie above said first and second grooves;
    said first and second grooves being shaped to guide a first one-half knot in the suture, and said third groove being shaped to guide a second one-half knot which is tightened against the first one-half knot to form a full knot when said movable shaft member is slid to said extended position; and
    said movable shaft member being positioned in a longitudinal channel in said stationary shaft member.

9. The device of claim 8 wherein said distal head passes distal to said stationary shaft member in said extended position.

* * * * *